Figure 1:
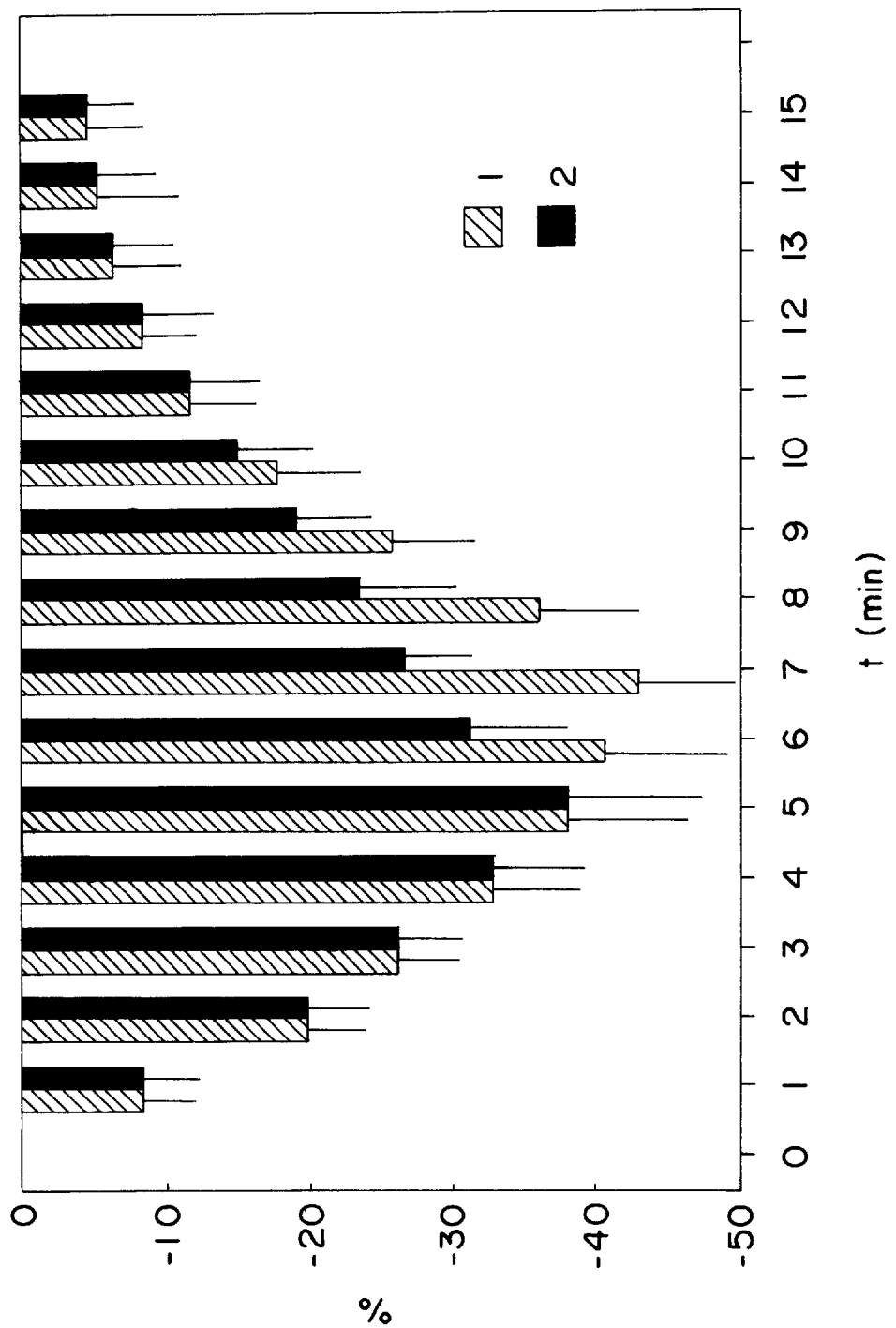

United States Patent [19]
Klopp et al.

[11] Patent Number: 5,814,301
[45] Date of Patent: Sep. 29, 1998

[54] USE OF PROSTACYCLIN DERIVATIVES TO PREVENT OR TO TREAT DISORDERS OF THE MICROCIRCULATORY SYSTEM WHEN X-RAY, NMR OR ULTRASONIC CONTRAST MEDIA ARE ADMINISTERED

[75] Inventors: Rainer Klopp; Wolfgang Niemer; Wolfgang Schippel; Werner Krause, all of Berlin, Germany

[73] Assignee: Schering Aktiengesellschaft, Berlin, Germany

[21] Appl. No.: 232,006

[22] PCT Filed: Oct. 22, 1992

[86] PCT No.: PCT/DE92/00904

§ 371 Date: Jun. 23, 1995

§ 102(e) Date: Jun. 23, 1995

[87] PCT Pub. No.: WO93/07875

PCT Pub. Date: Apr. 29, 1993

[30] Foreign Application Priority Data

Oct. 22, 1991 [DE] Germany .......... 41 35 193.2

[51] Int. Cl.$^6$ .................. A61K 31/557
[52] U.S. Cl. .......... 424/9.3; 424/9.43; 424/9.5; 514/530; 514/169
[58] Field of Search .......... 424/9.3, 9.43, 424/9.5; 514/469, 530, 573

[56] References Cited

U.S. PATENT DOCUMENTS

| 4,820,732 | 4/1989 | Shell et al. |
| 4,955,878 | 9/1990 | See et al. ......... 514/530 |
| 5,010,065 | 4/1991 | Skuballa et al. ......... 514/530 |
| 5,049,582 | 9/1991 | Adler et al. ......... 514/530 |

FOREIGN PATENT DOCUMENTS

| A-0217419 | 4/1987 | European Pat. Off. |
| A-0385859 | 9/1990 | European Pat. Off. |
| A-0407148 | 1/1991 | European Pat. Off. |
| WO-A-8904808 | 2/1986 | WIPO. |
| WO-A-8904828 | 6/1989 | WIPO. |

OTHER PUBLICATIONS

Y. Uchida, "Effects of a prostaglandin 12 analog, ZK 36734 on recurring reduction of coronary blood flow", *Chemical Abstracts*, vol. 100, No. 13, Abstract No. 97374u.

L. Caspary, "Intravenous infusion of iloprost in arterial occlusive disease: dose–dependent effects on skin microcirculation", *Eur. J. Clin. Pharmacol.*, vol. 41, No. 2 (1991).

CW. Abbottsmith, "Fate of patients with acute myocardial infarction with patency of the infarct–related vessel achieved with successful thrombolysis versus rescue angioplasty", *J. Am. Coll. Cardiol.*, vol. 16, No. 4 (Oct. 1990), pp. 770–778.

*Primary Examiner*—Robert Gerstl
*Attorney, Agent, or Firm*—Millen, White, Zelano & Branigan, P.C.

[57] ABSTRACT

Use of a prostacyclin derivative of general formula I

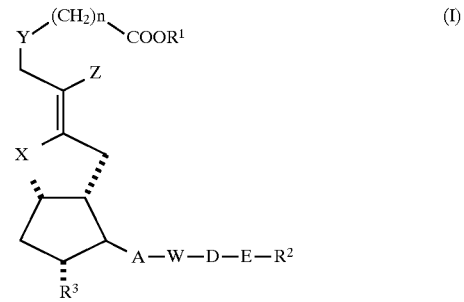

in which $R^1$, X, Y, Z, A, W, D, E, $R^2$ and $R^3$ may have different meanings, for the production of a pharmaceutical agent to prevent or to treat disorders of the microcirculatory system when x-ray, ultrasonic or NMR contrast media are administered.

7 Claims, 6 Drawing Sheets

USE OF PROSTACYCLIN DERIVATIVES TO PREVENT OR TO TREAT DISORDERS OF THE MICROCIRCULATORY SYSTEM WHEN X-RAY, NMR OR ULTRASONIC CONTRAST MEDIA ARE ADMINISTERED

Contrast media are essential auxiliary agents in medical diagnosis. They make possible increasingly greater contrast in the pictures obtained as well as better detection of the various tissues and organs. Among other things, they are used in x-ray, ultrasonic and magnetic resonance processes. There are a multitude of undesirable side effects with respect to this very useful application, such as, for example, changes of endothelial cells, damage of the erythrocytes, influencing of the blood clotting system, disorder of the microcirculatory system up to complete hemostasis, increase of the already existing disorder of the microcirculatory system in the pathogenic tissue, changes of the blood-brain barrier or negative influencing of the blood pressure. The disorder of the microcirculatory system is especially important. The microcirculatory system is functionally the most important part of the circulatory system. The metabolism takes place in the area of the microcirculatory system. In the case of a disorder of the microcirculatory system, among others, reduction of the blood cell-perfused branch points, increase of adhesions of the blood cells on the inner wall of the venules and erythrocyte aggregation can be observed. The arteriolar vasomotion is also impaired. A number of diseases, not only of the cardiovascular system, are attributable to disorders of the microcirculatory system. Therefore, it is absolutely desirable to avoid or to treat immediately a disorder of the microcirculatory system as a consequence of administering a contrast medium.

A multitude of pharmacological effects are already known from chemically stable prostacyclin derivatives.

It has now been found, surprisingly, that the prostacyclin derivatives of this invention maintain or restore the microcirculatory system to a significant extent when administered shortly before or after administering x-ray, ultrasonic or NMR contrast media or when jointly administered with said contrast media.

The invention relates to the use of a prostacyclin derivative or of the corresponding β-cyclodextrin clathrate or of the form encapsulated with liposomes for the production of a pharmaceutical agent to prevent or to treat disorders of the microcirculatory system when x-ray, NMR or ultrasonic contrast media are administered.

This invention preferably relates to the use of one or more prostacyclin derivatives of general formula I (I)

in which $R^1$ means hydrogen or a $C_1$–$C_4$ alkyl radical, n means 0 to 3,

X, Y, independently of one another, mean a —$CH_2$ group or an oxygen atom,

Z means hydrogen, fluorine or CN,

A means a trans —CH=CH— or a —C≡C— group,

W means a hydroxymethylene group that is free or functionally modified on the hydroxy group, in which the hydroxy group can be in α- or β-position, D means a straight-chain or branched, saturated $C_1$–$C_5$ alkylene group, E means a —C≡C— group $R^2$ means a $C_1$ $C_2$ alkyl group, $R^3$ means a free or functionally modified hydroxy group, and if $R^1$ means hydrogen, its salts with physiologically compatible bases, as well as its α-, β- or γ-cyclodextrin clathrates as well as its form encapsulated with liposomes or ataprost, beraprost, BW-15AU, ciprostene, CS 570, FCE 22509, naxaprostene, RS-93427, SC 39902 or taprostene for the production of a pharmaceutical agent to prevent or to treat disorders of the microcirculatory system when x-ray, ultrasonic or NMR contrast media are administered.

This invention especially preferably relates to the use of the prostacyclin derivatives iloprost, iloprost-clathrate, cicaprost, cicaprost-clathrate, eptaloprost or eptaloprost-clathrate.

As alkyl groups in $R^1$, straight- or branched-chain alkyl groups with 1–4 C atoms are to be considered, such as, for example, methyl, ethyl, propyl, isopropyl, butyl, isobutyl, tert-butyl. Alkyl groups $R^1$ can optionally be substituted by halogen atoms, methoxy, ethoxy, phenyl or ($C_1$–$C_2$)-dialkylamines.

As substituents, there can be mentioned, for example, fluorine, chlorine or bromine atoms, phenyl, dimethylamine, diethylamine, methoxy or ethoxy. Preferred alkyl groups $R^1$ are methyl, ethyl, dimethylaminopropyl.

As alkyl group $R^2$, methyl and ethyl can be mentioned.

The hydroxy groups in $R^3$ and W can be present as free hydroxy groups, in which the hydroxy group in W is preferably in α-position or can be functionally modified, for example, by etherification or esterification. Free hydroxy groups are preferred. As ether or acyl radicals, the radicals known to one skilled in the art are considered. Preferred are easily cleavable ether radicals, such as, for example, tetrahydropyranyl, tetrahydrofuranyl, α-ethoxyethyl, trimethylsilyl, dimethyl-tert-butylsilyl, diphenyl-tert-butylsilyl or tribenzylsilyl.

As acyl radicals, there can be mentioned, for example, acetyl, propionyl, butyryl or benzoyl.

As alkylene group D, straight-chain or branched, saturated alkyl groups with 1–5 C atoms are considered, for example, methylene, ethylene, 1- or 2-propylene, ethylethylene, trimethylene, tetramethylene, pentamethylene, 1-methyldimethylene, 1-methyltrimethylene, 1-methyltetramethylene.

Inorganic and organic bases are suitable for salt formation with the free acids ($R^1$=H), as they are known to one skilled in the art for the formation of physiologically compatible salts. For example, there can be mentioned: alkali hydroxides, such as sodium or potassium hydroxide, alkaline-earth hydroxides, such as calcium hydroxide, ammonia, amines such as ethanolamine, diethanolamine, triethanolamine, N-methylglucamine, morpholine, tris (hydroxymethyl)methylamine, etc.

The clathrates with α-, β- or γ-cyclodextrin are obtained analogously to the instructions of WO 87/05294. Preferred clathrates are those with β-cyclodextrin.

Liposomes are produced, e.g., according to the process described in "Pharmazie in unserer Zeit [Pharmaceutics in Our Time] 11, 98 (1982)."

The production of the compounds of formula I is described in detail in EP 2234 B1 and EP 11591 B1.

In EP 11591 B1, the following pharmacological properties are described for prostacyclin derivatives of formula I:

Reduction of the peripheral arterial and coronary vascular resistance, inhibition of the platelet aggregation and dissolution of platelet clots, myocardial cytoprotection and thus reduction of the systemic blood pressure without simultaneously reducing cardiac output and coronary blood circulation; treatment of stroke, prophylaxis and treatment of coronary heart diseases, coronary thrombosis, myocardial infarction, peripheral arteriopathies, arteriosclerosis and thrombosis, shock treatment, inhibition of bronchoconstriction, inhibition of gastric acid secretion and cytoprotection of the stomach and intestinal mucous membrane; antiallergic properties, reduction of the pulmonary vascular resistance and of the pulmonary blood pressure, promotion of renal circulation, use instead of heparin or as adjuvant in the dialysis or hemofiltration, preserving of dried blood plasma, especially of dried blood platelets, inhibition of labor pains, treatment of toxemia of pregnancy, increase of the cerebral circulation, etc. In addition, the new prostaglandin analogs have antiproliferative properties.

In EP 86404 B1, the use of carbacyclins to prevent and treat ischemic attacks of the central nervous system, for cytoprotection in the liver and in the pancreas as well as the combination with β-blockers or diuretics is described. From WO 86/00808, the cytoprotection of the kidneys as well as the suitability of the prostacyclin derivatives of formula I to treat organs to be transplanted is known. In DE 35 26 362 A1, the combination of the prostacyclin derivatives of formula I with thromboxane antagonists for use in the case of thrombotic or thromboembolic syndromes is described.

From DE 35 44 663 A1, the combination of prostacyclin derivatives of formula I with fibrinolytic agents to prevent recurring thromboses after a thrombosis is known.

In DE 36 08 088 A1, the clathrates of the carbacyclin derivatives of formula I are described, From DE 36 31 169 A1, the topical form of administration is known in addition to the forms of administration described in EP 11591 B1.

The use of prostacyclin derivatives of formula I claimed within the scope of this invention is not mentioned in any of the above laid-open specifications or patents.

Completely surprisingly, studies of the animal model have shown that the claimed compounds can be used successfully to treat or to avoid disorders of the microcirculatory system by administration of x-ray, ultrasonic or NMR contrast media.

The disorders of microcirculatory system observed with the use of a contrast medium in an animal test, such as, e.g., drastic reduction of the blood cell-perfused branch points in the microvascular network, increase of aggregated erythrocytes, increased adhesions of white blood cells to the inner wall of the venules as well as impairment of the arteriolar vasomotion, are especially pronounced in the second and seventh minutes after the contrast medium is administered, which coincides with the clinical empirical findings on side effects of and incidents with contrast media (so-called immediate reaction after about 2 minutes or so-called delayed reaction after about 7 minutes).

When particle-containing contrast media are administered as they occur with several ultrasonic contrast media or NMR contrast media, an administration of the claimed compounds to treat or to avoid disorders of the microcirculatory system appears useful even though the disorder of the microcirculatory system observed in the study of healthy tissue is relatively small. For it must not be overlooked that with angiopathological conditions, and only then, does in general a study with administration of contrast medium take place, that could even intensify existing disorders in the contrast medium particles flooded in the microcirculatory system.

The administration of the claimed compounds before, simultaneously with and after administration of contrast media produces a substantial avoidance or a decidedly reduced disorder of the microcirculatory system connected with a faster restoration of the microperfusion.

The claimed compounds can be administered topically or intravascularly (i.a., i.v.). The contrast medium is administered intravascularly (i.a., i.v.).

The dose of the prostacyclin derivatives is 1.6–0.0004 μg/kg of body weight, preferably 1.2 –0.0004 μg/kg of body weight.

For the simultaneous administration of prostacyclin derivatives with contrast media, this invention further relates to the combination of prostacyclin derivatives with contrast media, in which prostacyclin derivatives and contrast media can be present in one or in separate dosage units.

X-ray, ultrasonic and NMR contrast media are suitable for the combination.

Preferred contrast media for the combination are iotrolan, iopromide, iohexene, iosimide, metrizamide, salts of amidoacetic acid, iotroxic acid, iopamidol, 5-hydroxyacetamido-2,4,6-triiodo-isophthalic acid-(2,3-dihydroxy-N-methylpropyl)(2hydroxyethyl)-diamide, 3-carbamoyl-5-[N-(2-hydroxyethyl)-acetamido]-2,4,6-triiodo-benzoic acid [(1RS,2SR)-2,3-dihydroxy-1-hydroxymethylpropyl]amide, dispersions of iodipamide ethyl ester, gadolinium DTPA, gadolinium DOTA, the gadolinium complex of 10[1-hydroxymethyl-2,3-dihydroxypropyl]-1,4,7-tris[(carboxymethyl)-1,4,7,10-tetraazacyclododecane], Pro Hance$^R$, Magnevist$^R$, omniscan$^R$, iron or manganese porphyrin chelates, stable magnetite dispersions, dispersions of galactose microparticles with or without additives in water, a galactose solution or dispersions of microspheres of enclosed air, especially cyanacrylates or albumin microspheres, Echovist$^R$, Levovist$^R$.

The dosage unit of the contrast media can be 1–350 mg of iodine/1 for x-ray contrast media, 1–1000 μg of particles/kg of body weight for ultrasonic contrast media and 0.01–0.5 mol for NMR contrast media. But these data can be only guide values, since the contrast medium dosage depends greatly on the desired use.

Prostacyclin derivatives, especially those mentioned under claim 2, are suitable for the combination.

The dose of prostacyclin derivatives for the combination lies in the range already indicated for the separate administration.

Should the physical properties of the contrast medium solutions or dispersions not assure the stability of the prostacyclin derivative over a long time, the combination in separate dosage units is preferred for these cases.

REFERENCE SYMBOLS

FIG. 1

Presentation of the percentage reduction of the blood cell-perfused branch points in the microvascular network in comparison to the initial conditions 1—Animal group 1, diatrizoate bolus 2—animal group 2, 5 minutes after diatrizoate administration, iloprost injection t—time in [minutes]

%—blood cell-perfused branch points

FIG. 2

Presentation of the percentage increase of the portion of aggregated erythrocytes in the total cell number in the microvascular network in comparison to the initial conditions 1, 2, t—see FIG. 1

%—portion of aggregated erythrocytes in [%]

FIG. 3

Presentation of the number of adhering blood cells on a defined inner wall surface of venules 1, 2, t—see FIG. 1

BZ—number of blood cells

A—defined inner wall surface of venules

Figure 4:
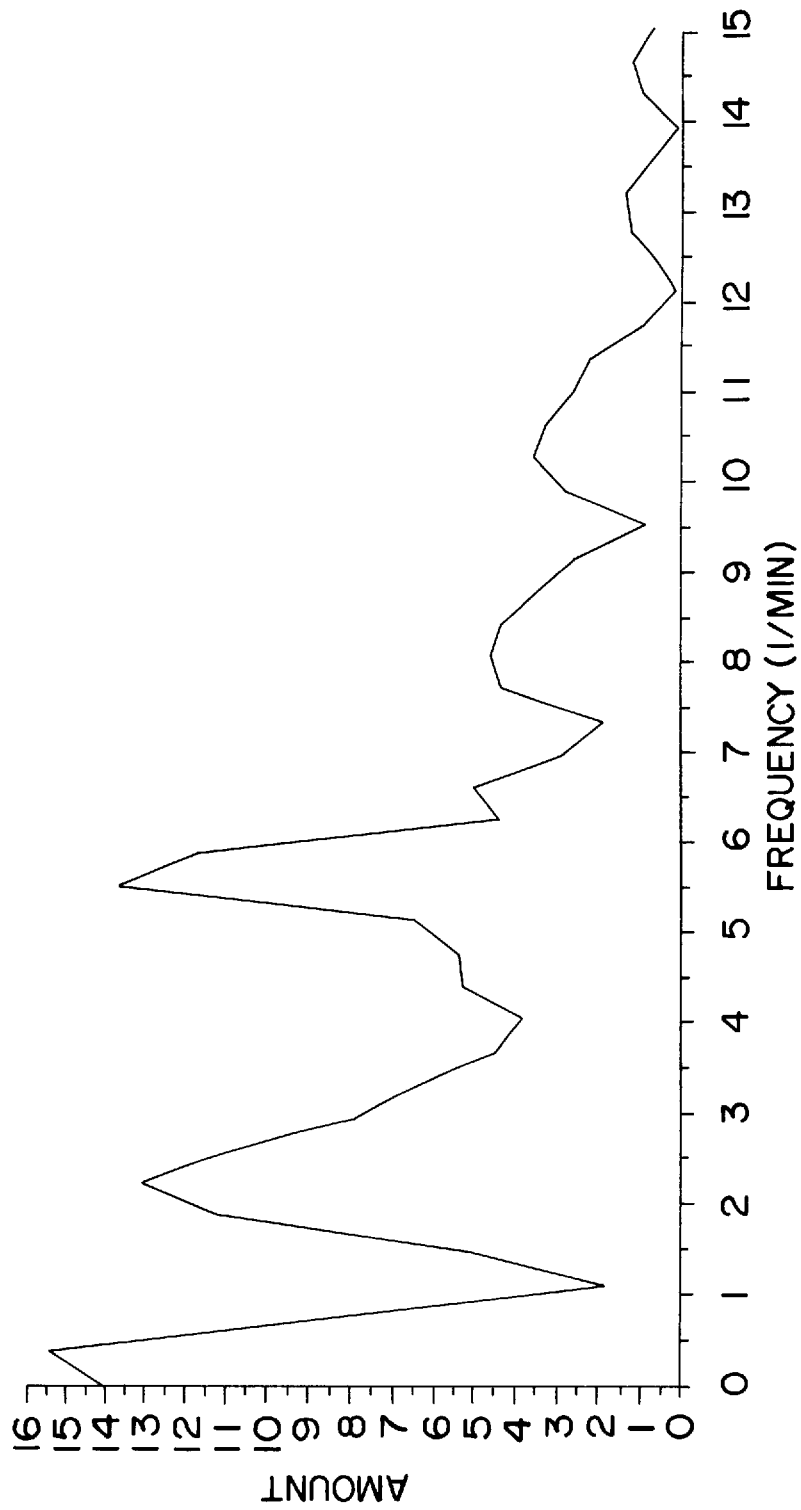
Figure 5:
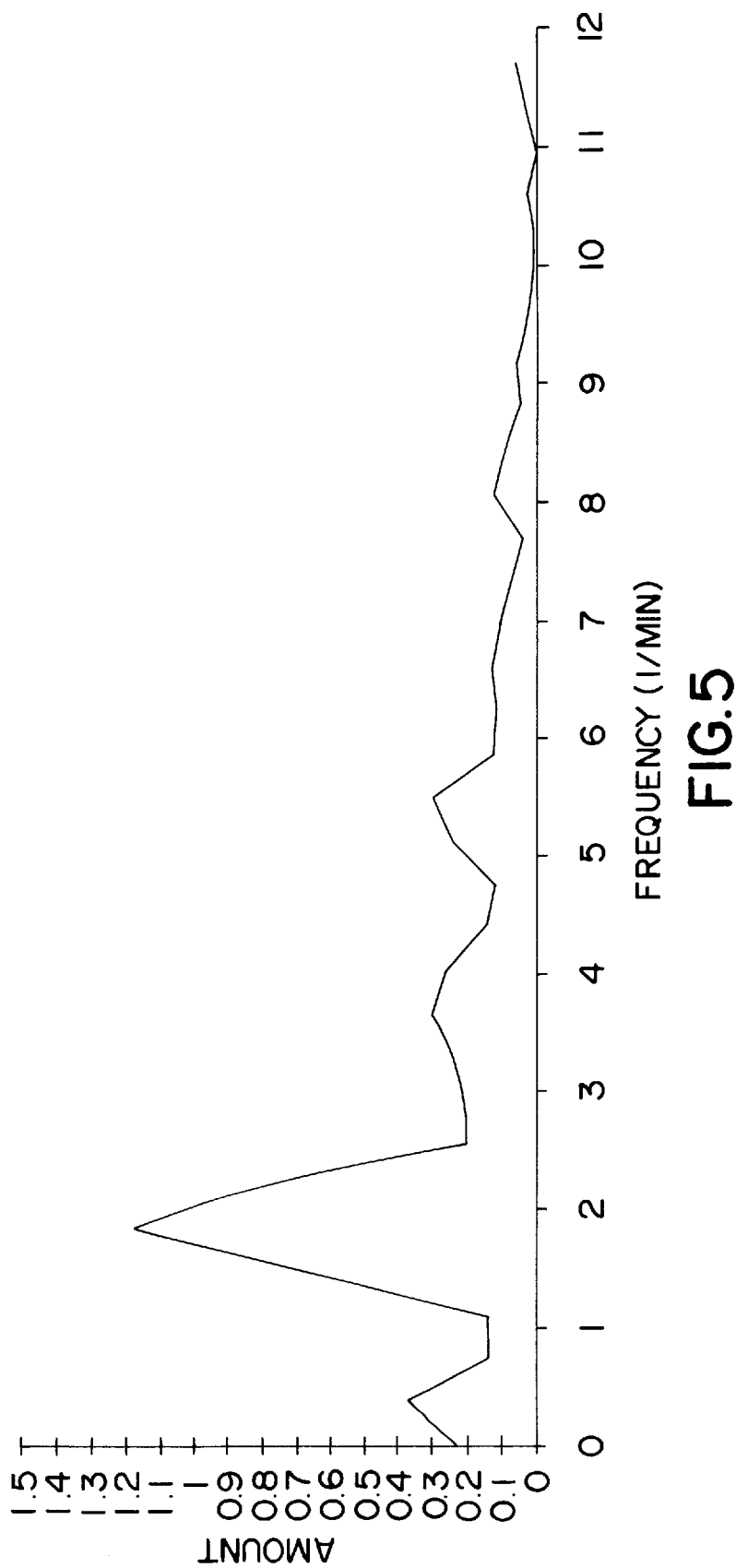
Figure 6:
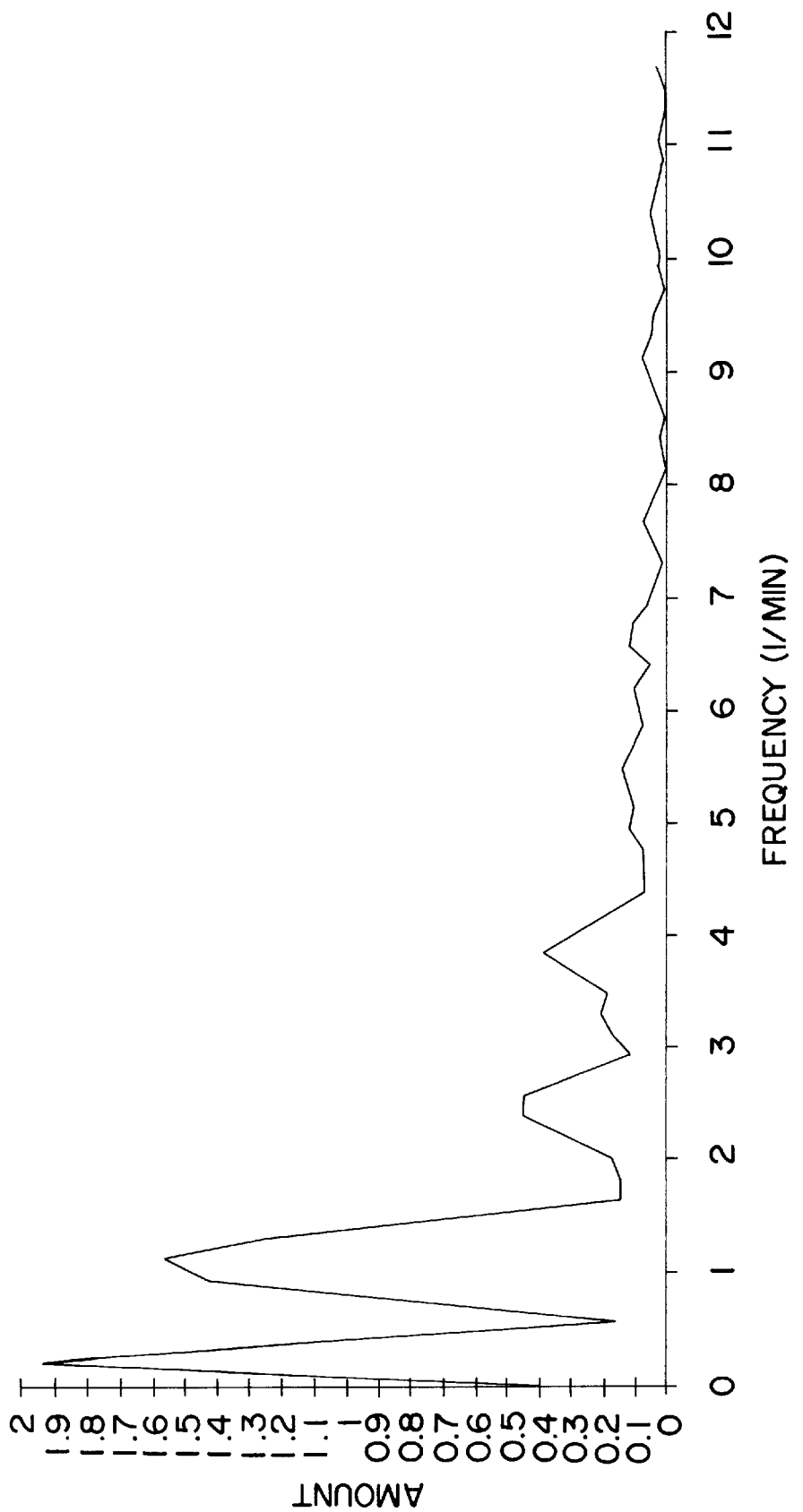

FIGS. 4, 5 and 6

Presentation of frequency spectra of the arteriolar vasomotion.

EXAMPLE 1

A microcatheter for intraarterial injection of the contrast medium is moved from the A. carotid communis up to the aortic arch in anesthetized rats of the Wistar-Schdowalde strain (anesthesia with urethane-chloralose mixture—i.p., i.m.—10% urethane in isotonic NaCl solution, 2% α-chloralose in isotonic NaCl solution; 0.6 ml/100 g of body weight as initial dose, 0.2 ml/100 g of body weight as maintenance dose if necessary). One-time injection of a body-temperature bolus of amidotrizoate/urografin with 600 mg of iodine/kg of body weight takes place. The injection time is 30 seconds. The administration of iloprost takes place 5 minutes after administration of contrast medium, with intraarterial administration by the same injection path as the contrast medium, with intravenous administration via V. femoralis and with topical administration via intestine/mesentery. The iloprost dose is 0.8–1.6 µg of iloprost/kg of body weight in 2.0 ml of solution/kg of body weight. With topical administration, 3 drops of this solution are used. The number of test animals is 45 with intraarterial administration, 25 with intravenous administration and 20 with topical administration. The control animals receive physiological common salt solution in the corresponding administration. The number of control animals is 12 with intraarterial and intravenous administration and 20 with topical administration.

Results

The assessment is performed on anesthetized animals under constant boundary conditions by combined incident light-transmitted light intravital microscopy on the exposed mesentery/intestine in thermostatted bath solution. The recording of data takes place usually in an interval of 5 minutes before the administration of contrast medium to 15 minutes after the administration of contrast medium every minute.

The blood cell-perfused branch points of the intestinal microflow increase by administration of iloprost. The comparison with the untreated control shows that iloprost clearly damps the disorders of the microcirculatory system induced by contrast medium in the clinically significant time interval of the 5th to 10th minutes p.a. of amidotrizoate and that a faster restoration of the physiological microperfusion is achieved.

FIG. 1 shows the percentage reduction of the blood cell-perfused branch points in the microvascular network of the mesentery with administration of contrast medium in comparison to the initial conditions as well as the effect of the iloprost administration. Two animal groups are compared: group 1 received a diatrizoate bolus at t=0 hours; after the diatrizoate bolus at t=0 hours, group 2 received an iloprost bolus of 0.8 µg/kg at t=5 hours. The trabecular presentation indicates average values x, the superposed lines standard deviation S.

The percentage portion of aggregated erythrocytes of the total cell number in the mesenteral network is greatly reduced by iloprost, i.e., the reduction of the number of aggregated erythrocytes is accelerated.

Figure 2:
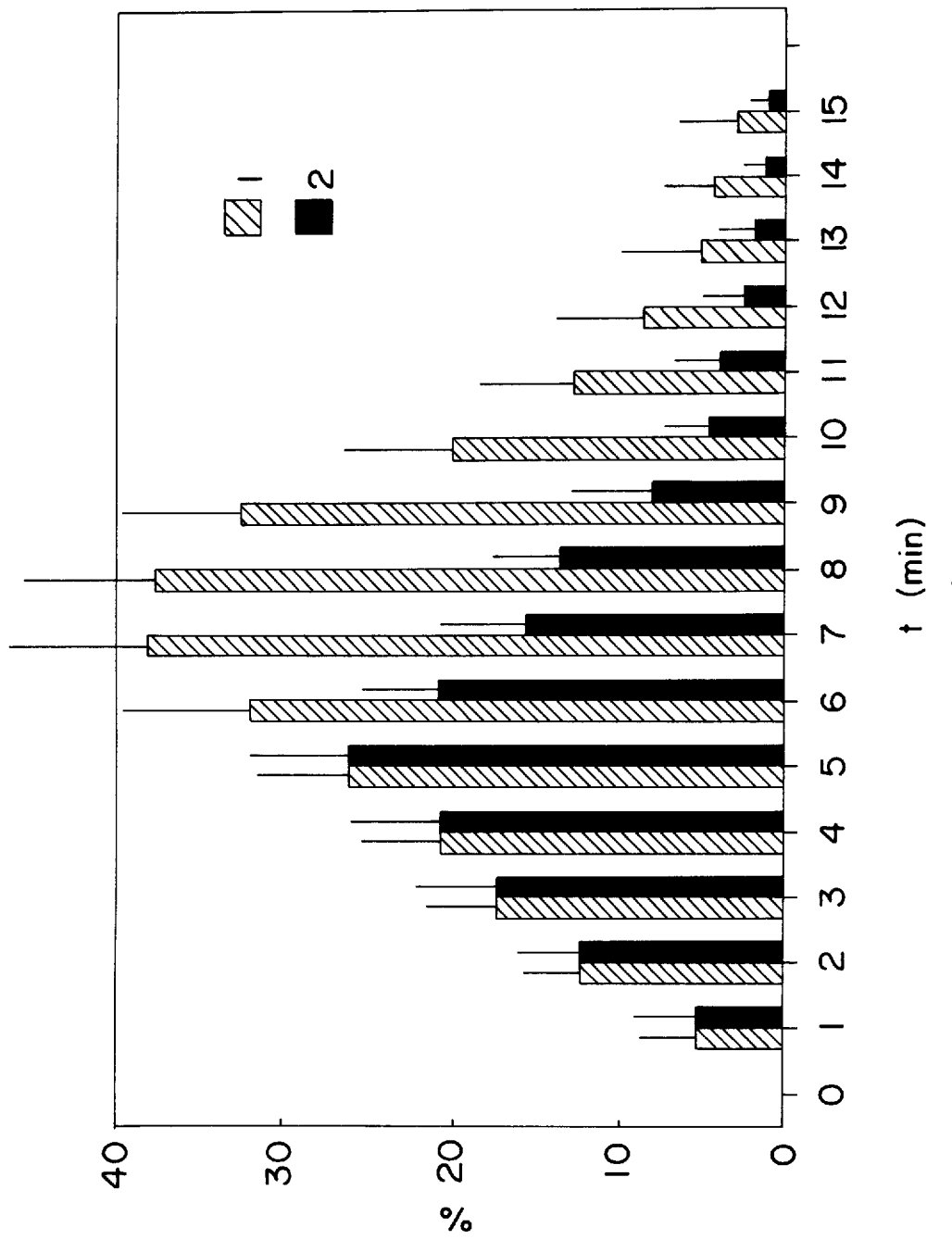

FIG. 2 shows the percentage increase of the portion of aggregated erythrocytes of the total cell number in the microvascular network of the mesentery with administration of contrast medium in comparison to the initial conditions as well as the effect of the iloprost administration. Animal groups 1 and 2 were treated as in the above test. The presentation of the average values or standard deviation takes place as in FIG. 1.

The reduction of the number of adhering white blood cells on the inside wall of the venules is greatly accelerated as by iloprost.

Figure 3:
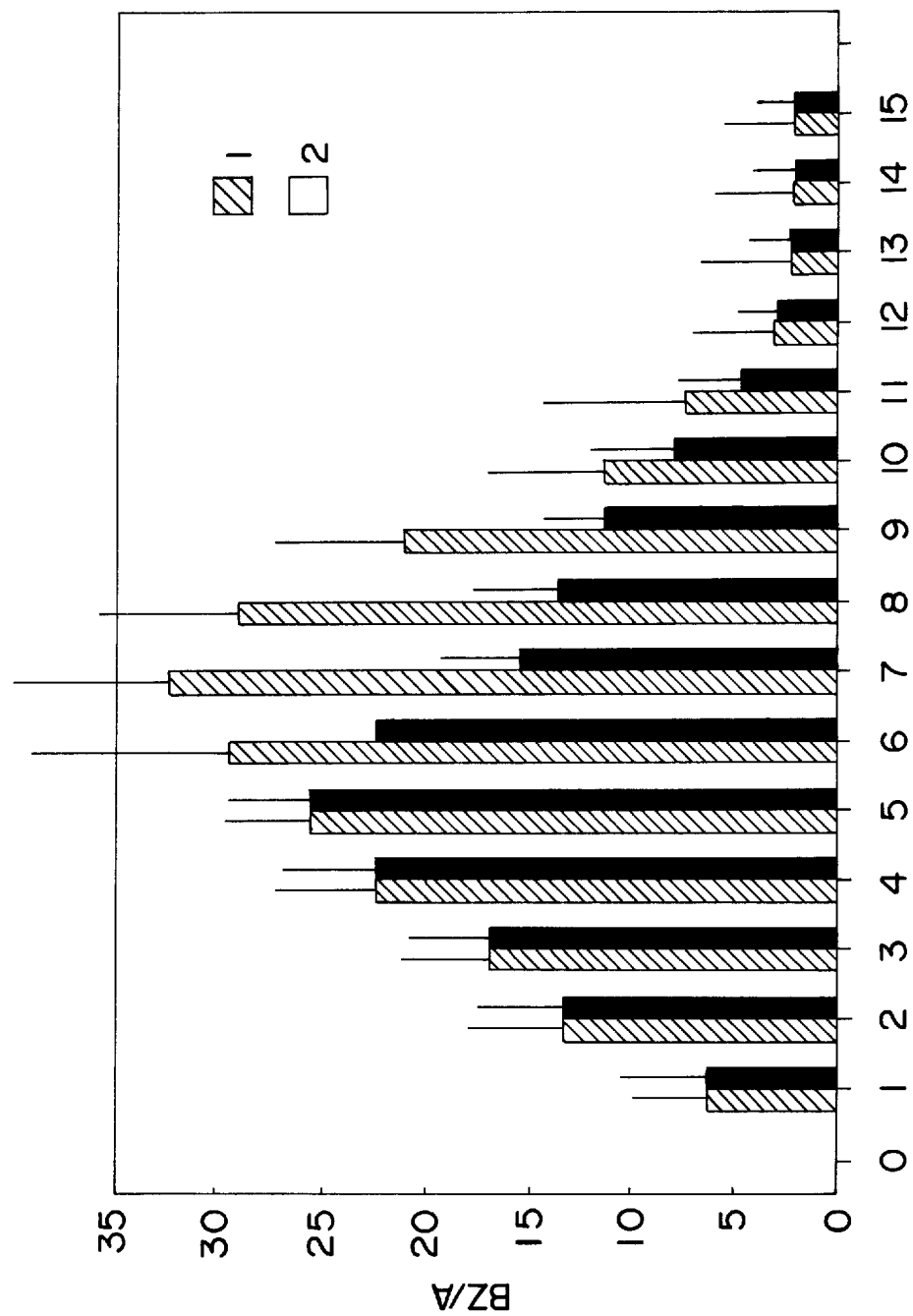

FIG. 3 shows the number of adhering blood cells on a defined inner wall surface of the venules of the mesentery as a function of time. Animal groups 1 and 2 were treated as in the above test. The presentation of the average values or standard deviation takes place as in FIG. 1.

EXAMPLE 2

A microcatheter for intravascular injection of the contrast medium either is moved in the A. carotid comm. up to the aortic arch (intraarterial injection) or introduced in the V. femoralis (intravenous injection) in anesthetized adult rats [body weight X=304.7 g (S=35.4 g)] of the Wistar strain (anesthesia with urethane-chloralose mixture—i.p., i.m.—10% urethane in isotonic NaCl solution, 2% α-chloralose in isotonic NaCl solution; 0.6 ml/100 g of body weight as initial dose, 0.2 ml/100 g of body weight as maintenance dose if necessary). One-time injection of a body-temperature bolus of diatrizoate/urografin with 600 mg of iodine/kg of body weight takes place. The injection time is 30 seconds. The administration of iloprost takes place 5 minutes after administration of contrast medium, with intravascular administration in the same injection path as the contrast medium or with topical administration via intestine/mesentery. The iloprost dose is 1.6–0.0004 µg of iloprost/kg of body weight in 2.0 ml of solution/kg of body weight. With topical administration, 3 drops of this solution are used. As comparison substance, physiological common salt solution with a suitable volume is administered. Because of the small differences of the body weights of the test animals, an almost identical bolus volume of about 1 ml can be administered in all test animals. The number of test animals is 10 per treatment group.

The following measurable variables (features) ate determined:

Number of the currently cell-perfused branch points in the microvascular network (%, percentage change of the number in comparison to the initial conditions);

number of aggregated erythrocytes in the microvascular stream bed (%, percentage portion of aggregated erythrocytes of the total cell number in the observed stream bed; as erythrocyte aggregation, a prolonged adhering of at least 2 to 3 erythrocytes is observed, in which the different types of aggregation are not differentiated);

number of adhering blood cells on the inner wall of the venules (BZ/A; number of blood cells, which adhere to the venule endothelium longer than 5 seconds—relative to a defined inner wall surface of venules A of 18000 $\mu^2$, which is given in a venule diameter $d_v=40$ $\mu$m by an axial venule length $l_v=140$ $\mu$);

arteriolar vasomotion (determination of the inner diameter of an arteriole with a diameter of about 45 $\mu$m on a specific site at each second in the observation interval of about 15 minutes; determination of the amplitude-frequency spectrum of the vasomotion oscillation).

The measurable variables, if not otherwise indicated, are determined in microvessels with diameters $\leq 40$ $\mu$m. The measurements of the microcirculatory features are made on the mesentery of the small intestine and on the mucous membrane of the small intestine itself in complete, in each case identical segments. For this purpose, the intestine is surgically exposed on the anesthetized and thermostated animal and evacuated in a bath solution thermostated at body temperature (equivalent to the intraperitoneal liquid).

The presentation of the microvascular network takes place with the help of an intravital microscopic examination unit in the combined incident light-transmitted light process on the intact organ with computer-assisted image manipulation and processing. The vital microscopic assessments are made with constant macrocirculatory boundary conditions.

Before the intravital microscopic measured value detection, in each case, an orienting survey of the complete microvascular network of the entire mesenteric or intestinal segment is obtained—including its other inflows and outflows, branching geometry and hierarchy and functional vessel identification. The anatomical vessel identification in the stained histological preparation takes place after the end of the test within the scope of the final histopathological study of all test animals. The recording of data takes place usually at an interval of 5 minutes before the administration of contrast medium to 10 minutes after the administration of contrast medium every minute.

Results

The number of blood cell-perfused branch points increases more quickly by administration of iloprost.

The portion of aggregated erythrocytes of the total blood cell number in the network decreases more quickly after administration of iloprost.

The number of blood cells adhering to the inner wall of the venules decreases by iloprost.

In the following table, measuring results in the above-described findings in the microvascular network of the mucous membrane of the small intestine are indicated. A diatrizoate bolus was injected in one animal group (column 1), a second group received an intravenous administration of 0.8 $\mu$g/kg of iloprost 5 minutes after injection of the diatrizoate bolus (column 2). x designates the average value, UG the lower limit and OG the upper limit of the confidence interval.

The frequency spectrum of the arteriolar vasomotion exhibits smaller deviations from the normal state by iloprost administration than in exclusive administration of contrast media (see FIG. 4–6).

FIG. 4 shows the frequency spectrum of a control animal;

FIG. 5 shows the frequency spectrum of an animal in the seventh minute after intravenous administration of diatrizoate and FIG. 6 shows the frequency spectrum of an animal, which was administered iloprost with a dose of 0.8 $\mu$g/kg 5 minutes after intravenous administration of diatrizoate in the same path of injection, in the seventh minute after administration of contrast medium, i.e., in the second minute after iloprost injection.

95% Confidence Intervals for Average Values of the Changes of Different Parameters (Features) of the Intestinal Microcirculatory System

| Feature | Administration of diatrizoate/urografin (value of the variable 7th min. p.i. minus the value of the variable in the 0 min.) | Administration of iloprost/ilomedin in the fifth min. p.i. of the contrast medium diatrizoate/urografin (value of the variable in the 7th min. p.i. of the contrast medium, i.e., 2nd min. p.i. of the iloprost, minus the value of the variable in the 0 min.) |
|---|---|---|
| Number of currently blood cell-perfused branch points in comparison to the initial conditions in % | x̄: −22.0<br>UG: −27.3<br>OG: −16.7 | −11.0<br>−19.8<br>−2.2 |
| Portion of aggregated red blood cells of the total cell count in the microvascular stream bed in % | x̄: 26.5<br>UG: 21.9<br>OG: 31.2 | 6.2<br>1.7<br>10.7 |
| Number of adhering blood cells BC at a specific inner wall surface of venules A = 18000$\mu^2$ (BC/A) | x̄: 19.5<br>UG: 16.3<br>OG: 22.7 | 6.4<br>−0.1<br>12.9 |

UG — lower limit
OG — upper limit
x̄ — average value

EXAMPLE 3

A microcatheter for intravascular injection of the contrast medium either is moved in the A. carotid comm. up to the aortic arch (intraarterial injection) or introduced in the V. femoralis (intravenous injection) in anesthetized adult rats [body weight X=304.7 g (S=35.4 g)] of the Wistar strain (anesthesia with urethane-chloralose mixture—i.p., i.m.— 10% urethane in isotonic NaCl solution, 2% α-chloralose in isotonic NaCl solution; 0.6 ml/100 g of body weight as initial dose, 0.2 ml/100 g of body weight as maintenance dose if necessary). One-time injection of a body-temperature bolus of diatrizoate/urografin with 600 mg of iodine/kg of body weight takes place. The injection time is 30 seconds. The administration of iloprost takes place simultaneously with the administration of contrast medium, with intravascular administration in the same injection path as the contrast medium or with topical administration via intestine/mesentery. The iloprost dose is 1.6–0.0004 $\mu$g of iloprost/kg of body weight in 2.0 ml of solution/kg of body weight. With topical administration, 3 drops of this solution are used. As comparison substance, physiological common salt solution with a suitable volume is administered. Because of the small differences of the body weights of the test animals, an almost identical bolus volume of about 1 ml can be administered in all test animals. The number of test animals is 10 per treatment group.

The following measurable variables (features) are determined:

Number of the currently cell-perfused branch points in the microvascular network (%, percentage change of the number in comparison to the initial conditions);

number of aggregated erythrocytes in the microvascular stream bed (%, percentage portion of aggregated erythrocytes of the total cell number in the observed stream bed; as erythrocyte aggregation, a prolonged adhering of at least 2 to 3 erythrocytes is observed, in which the different types of aggregation are not differentiated);

number of adhering blood cells on the inner wall of the venules (BZ/A; number of blood cells, which adhere to the venule endothelium longer than 5 seconds—relative to a defined inner wall surface of venules A of 18000 $\mu^2$, which is given in a venule diameter $d_v=40$ $\mu$m by an axial venule length $l_v=140$ $\mu$).

The measurable variables are, if not otherwise indicated, in microvessels with a diameter of about 45 $\mu$m at a specific site at every second in the observation interval of about 15 minutes: determination of the amplitude-frequency spectrum of the vasomotion oscillation).

The measurable variables, if not otherwise indicated, are determined in microvessels with diameters $\leq 40$ $\mu$m. The measurements of the microcirculatory features are made on the mesentery of the small intestine and on the mucous membrane of the small intestine itself in complete, in each case identical segments. For this purpose, the intestine is surgically exposed on the anesthetized and thermostated animal and evacuated in a bath solution thermostated at body temperature (equivalent to the intraperitoneal liquid).

The presentation of the microvascular network takes place with the help of an intravital microscopic examination unit in a combined incident light-transmitted light process on the intact organ with computer-assisted image manipulation and processing. The vital microscopic assessments are made with constant macrocirculatory boundary conditions.

Before the intravital microscopic measured value detection, in each case an orienting survey of the complete microvascular network of the entire mesenteric or intestinal segment is obtained—including its further inflows and outflows, branching geometry and hierarchy and functional vessel identification. The anatomical vessel identification in the stained histological preparation takes place after the end of the test within the scope of the final histological study of all test animals. The recording of the data takes place usually at an interval of 5 minutes before the administration of contrast medium to 10 minutes after the administration of contrast medium every minute.

Results

The number of blood cell-perfused branch points increases more quickly by administration of iloprost.

The portion of aggregated erythrocytes of the total blood cell number in the network decreases more quickly after administration of iloprost.

The number of blood cells adhering to the inner wall of the venules decreases by iloprost.

In the following table, measuring results for the above-described findings in the microvascular network of the mucous membrane of the small intestine are indicated. An animal group was injected with a diatrizoate bolus (column 1), a second group received an intravenous administration of 0.8 $\mu$g/kg of iloprost simultaneously with the injection of the diatrizoate bolus (column 2). x designates the average value, UG the lower limit and OG the upper limit of the confidence interval.

The frequency spectrum of the arteriolar vasomotion exhibits smaller deviations from the normal state by iloprost administration than with exclusive administration of contrast media.

95% Confidence Intervals for Average Values of the Changes of Different Parameters (Features) of the Intestinal Microcirculatory System

| Feature | Administration of diatrizoate/uro-grafin (value of the variable 7th min. p.i. minus the value of the variable in the 0 min.) | Administration of iloprost/ilomedin simultaneously with the contrast medium diatrizoate/uro-grafin (value of the variable in the 7th min. p.i. of the contrast medium, i.e., 2nd min. p.i. of the iloprost, minus the value of the variable in the 0 min.) |
|---|---|---|
| Number of currently blood cell-perfused branch points in comparison to the initial conditions in % | x̄: −22.0<br>UG: −27.3<br>OG: −16.7 | −10.4<br>−17.9<br>−2.9 |
| Portion of aggregated red blood cells of the total cell count in the microvascular streain bed in % | x̄: 26.5<br>UG: 21.9<br>OG: 31.2 | 5.7<br>2.1<br>9.2 |
| Number of adhering blood cells BC on a specific inner wall surface of venules A = 18000$\mu^2$ (BC/A) | x̄: 19.5<br>UG: 16.3<br>OG: 22.7 | 5.8<br>0.4<br>11.2 |

UG — lower limit
OG — upper limit
x̄ — average value

We claim:

1. A method for the prevention or treatment of disorders of the microcirculatory system occurring on administration of X-ray, NMR or ultrasonic contrast media, comprising administering, in conjunction with such contrast media, a compound of formula I

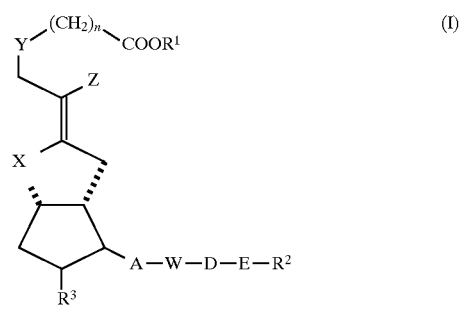

in which
 $R^1$ means hydrogen or a $C_1$–$C_4$ alkyl radical,
 n means 0 to 3,
 X, Y, independently of one another, mean a —$CH_2$ group or an oxygen atom,
 Z means hydrogen, fluorine or CN,
 A means a trans —CH═CH— or a —C≡C— group,
 W means a hydroxymethylene group that is free or functionally modified on the hydroxy group, in which the hydroxy group can be in α- or β-position.
 D means a straight-chain or branched, saturated $C_1$–$C_5$, alkylene group,
 E means a —C≡C— group,
 $R^2$ means a $C_1$–$C_2$ alkyl group,
 $R^3$ means a free or functionally modified hydroxy group, or if $R^1$ means hydrogen, a salt thereof with physiologically compatible bases, or a α-, β- or γ-cyclodextrin clathrate or a compound of formula I encapsulated with liposomes.

2. A method according to claim 1, wherein the compound of formula I is ataprost, beraprost, BW-15AU, ciprostene, CS 570, FCE 22509, naxaprostene, RS-93427, SC 39902 or taprostene.

3. A method according to claim 1, wherein the compound of formula I is iloprost or iloprost-clathrate.

4. A method according to claim 1, wherein the compound of formula I is cicaprost or cicaprost-clathrate.

5. A method according to claim 1, wherein the compound of formula I is eptaloprost-clathrate.

6. A method according to claim 1, wherein the prostacyclin derivative is 5-[(E)-(1S,5S,6S,7R)-7-hydroxy-6-[(3S,4S)-3-hydroxy-4-methyl-1,6-nonadiinyl]-bicyclo[3.3.0]-oct-3-ylidene]-pentanoic acid or the corresponding clathrate.

7. A method according to claim 1, wherein the prostacyclin derivative is 5-[(E)-(1S,5S,6S,7R)-7-hydroxy-6[-(3S,4S)-3-hydroxy-4-methyl-1,6-nonadiinyl]-bicyclo[3.3.0]-oct-3-ylidene]-5-fluoro-3-oxa-pentanoic acid or the corresponding clathrate.

* * * * *